United States Patent
Kim et al.

(10) Patent No.: US 9,742,032 B2
(45) Date of Patent: Aug. 22, 2017

(54) COMPOUND AND ELECTROLYTE OF LITHIUM SECONDARY BATTERY CONTAINING THE SAME

(71) Applicant: SK Innovation Co., Ltd., Seoul (KR)

(72) Inventors: Jin Sung Kim, Daejeon (KR); Cheol Woo Kim, Daejeon (KR); Seung Yon Oh, Daejeon (KR); Kwang Kuk Lee, Daejeon (KR); Seong Il Lee, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 14/855,438

(22) Filed: Sep. 16, 2015

(65) Prior Publication Data
US 2016/0087309 A1    Mar. 24, 2016

(30) Foreign Application Priority Data
Sep. 18, 2014 (KR) .......................... 10-2014-0124207

(51) Int. Cl.
| | | |
|---|---|---|
| *H01M 10/0567* | (2010.01) | |
| *H01M 10/0568* | (2010.01) | |
| *H01M 10/0569* | (2010.01) | |
| *C07D 319/12* | (2006.01) | |
| *C07D 321/08* | (2006.01) | |
| *H01M 10/052* | (2010.01) | |

(52) U.S. Cl.
CPC ...... *H01M 10/0567* (2013.01); *C07D 319/12* (2013.01); *C07D 321/08* (2013.01); *H01M 10/0568* (2013.01); *H01M 10/0569* (2013.01); *H01M 10/052* (2013.01)

(58) Field of Classification Search
CPC ........ H01M 10/0567; H01M 10/0568; H01M 10/0569; C07D 319/12; C07D 321/08
See application file for complete search history.

(56) References Cited

U.S. PATENT DOCUMENTS

| 4,525,540 A | * | 6/1985 | Weinstein ............ C07D 317/32 |
|---|---|---|---|
| | | | 525/327.2 |
| 5,879,834 A | | 3/1999 | Mao |

FOREIGN PATENT DOCUMENTS

| JP | 09-227551 | * | 9/1997 |
|---|---|---|---|
| JP | 2002260725 A | | 9/2002 |
| JP | 2013-175454 | * | 9/2013 |
| JP | 2015-103360 | * | 6/2015 |

OTHER PUBLICATIONS

Itaya, T., Iida, T., Gomyo, Y., Natsutani, I., Ohba, M.-Efficient Synthesis and Hydrolysis of Cyclic Oxalate Esters of Glycols, Chem. Pharm.Bull 50(3), pp. 346-353, 2002.*
Machine translation of JP09-227551, published on Sep. 2, 1997.*
Machine translation of JP2013-175454, published on Sep. 5, 2013.*
Machine translation of JP2015-103360, published on Jun. 4, 2015.*
Iida, T., Itaya, T-Cyclocondensation of Oxalyl Chloride with 1,2-Glycols, Tetrahedron vol. 49, No. 46, pp. 10511-10530, 1993.*

* cited by examiner

*Primary Examiner* — Anca Eoff
(74) *Attorney, Agent, or Firm* — The Webb Law Firm

(57) ABSTRACT

Provided are a novel compound, an electrolyte for a lithium secondary battery containing the same, and a lithium secondary battery containing the electrolyte for a lithium secondary battery according to the present invention. The electrolyte for a secondary battery according to the present invention may have significantly excellent high-temperature stability, low-temperature discharge capacity, and life cycle characteristics.

14 Claims, No Drawings

COMPOUND AND ELECTROLYTE OF LITHIUM SECONDARY BATTERY CONTAINING THE SAME

CROSS-REFERENCE TO RELATED APPLICATION

This application claims priority to Korean Patent Application No. 10-2014-0124207 filed Sep. 18, 2014, the disclosure of which is hereby incorporated in its entirety by reference.

TECHNICAL FIELD

The following disclosure relates to a novel compound and an electrolyte for a lithium secondary battery containing the same, and more particularly, to a novel compound capable of being used as an additive of an electrolyte for a lithium secondary battery, an electrolyte for a lithium secondary battery containing the same, and a lithium secondary battery using the electrolyte for a lithium secondary battery as described above.

BACKGROUND

Recently, as portable electronic devices have widely spread, in accordance with miniaturization, thinness, and lightness of the portable electronic devices, research into a secondary battery used as a source of these portable electronic devices, which may have a small size and a light weight and be charged and discharged for a long period of time, has been actively conducted.

The lithium secondary battery, which generates electrical energy by oxidation-reduction reactions when lithium ions are co-intercalated into and deintercalated from an anode and a cathode, is manufactured by using a material capable of intercalating and deintercalating lithium ions as the anode and the cathode, and filling an organic electrolyte or polymer electrolyte between the cathode and the anode.

An example of an organic electrolyte widely used at the present time includes ethylene carbonate, propylene carbonate, dimethoxyethane, gamma butyrolactone, N,N-dimethylformamide, tetrahydrofuran, acetonitrile, or the like. However, generally, since the organic electrolyte as described above may be easily volatilized and have high flammability, at the time of applying the organic electrolyte to a lithium ion secondary battery, a safety problem, for example, ignition due to an internal short-circuit when heat is generated in the battery by over-charge or over-discharge, or the like, may occur at a high temperature.

Further, at the time of initial charge of the lithium secondary battery, lithium ions released from a lithium metal oxide, which is a cathode, move to a carbon electrode, which is an anode, to thereby be intercalated into carbon. In this case, since lithium has high reactivity, while a surface of carbon particles, which is an anode active material, and an electrolyte react with each other, a coating film referred to as a solid electrolyte interface (SEI) film is formed on a surface of the anode.

Performance of the lithium secondary battery significantly depends on a configuration of the organic electrolyte and the SEI film formed by a reaction of the organic electrolyte and the electrode.

That is, the formed SEI film may suppress side reactions of a carbon material and an electrolyte solvent, for example, decomposition of the electrolyte on the surface of the carbon particle, which is the anode, prevent disintegration of an anode material caused by co-intercalation of the electrolyte solvent into the anode material, and serve as a lithium ion tunnel, thereby minimizing deterioration in performance of the battery.

Therefore, various researches for developing a novel organic electrolyte containing an additive in order to solve the above-mentioned problem have been conducted.

For example, a non-aqueous lithium ion battery capable of preventing over-charge current and a thermal runaway phenomenon caused by the over-charge current by using an aromatic compound such as biphenyl has been disclosed in Japanese Patent No. 2002-260725. In addition, a method of improving safety of a battery by adding a small amount of an aromatic compound such as biphenyl, 3-chlorothiophene, or the like, to increase an internal resistance by electrochemical neutralization in an abnormal over-voltage state has been disclosed in U.S. Pat. No. 5,879,834.

However, research for improving safety of a lithium secondary battery at a high temperature and a low temperature while maintaining a high capacity retention rate has been still demanded.

RELATED ART DOCUMENT

Patent Document (Patent Document 1) Japanese Patent No. 2002-260725

(Patent Document 2) U.S. Pat. No. 5,879,834

SUMMARY

An embodiment of the present invention is directed to providing a novel compound having excellent high-temperature and low-temperature characteristics while properly maintaining basic performances such as high-rate charge and discharge characteristics, life cycle characteristics, and the like, an electrolyte for a lithium secondary battery containing the same, and a lithium secondary battery using the electrolyte for a lithium secondary battery according to the present invention.

In one general aspect, there is provided a novel compound represented by the following Chemical Formula 1, which is used as an additive of an electrolyte for a lithium secondary battery in order to improve characteristics of a lithium secondary battery.

[Chemical Formula 1]

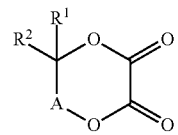

(In Chemical Formula 1, $R^1$ to $R^4$ are each independently hydrogen, cyano, halo (C1-C10)alkyl, (C1-C10)alkyl, (C1-C10)alkoxy, or (C1-C10)alkoxycarbonyl; and A is a single bond or $-(CR^3R^4)_n-$, n being an integer of 1 to 3.)

The compound represented by Chemical Formula 1 may be represented by the following Chemical Formula 2 or 3.

[Chemical Formula 2]

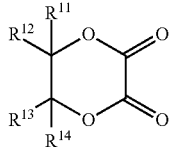

[Chemical Formula 3]

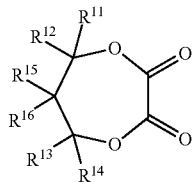

(In Chemical Formulas 2 and 3, $R^{11}$ to $R^{16}$ are each independently hydrogen, cyano, halo (C1-C10)alkyl, (C1-C10)alkyl, (C1-C10)alkoxy, or (C1-C10)alkoxycarbonyl.)

In Chemical Formulas 2 and 3, R11 to R16 may be each independently hydrogen, cyano, halo(C1-C10)alkyl, (C1-C10)alkyl, (C1-C10)alkoxy, or (C1-C10)alkoxycarbonyl.

In another general aspect, an electrolyte for a lithium secondary battery contains:

a lithium salt;

a non-aqueous organic solvent; and a compound represented by the following Chemical Formula 1.

[Chemical Formula 1]

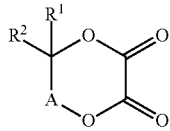

(In Chemical Formula 1, $R^1$ to $R^4$ are each independently hydrogen, cyano, halo (C1-C10)alkyl, (C1-C10)alkyl, (C1-C10)alkoxy, or (C1-C10)alkoxycarbonyl; and A is a single bond or —$(CR^3R^4)_n$—, n being an integer of 1 to 3.)

Preferably, the compound represented by Chemical Formula 1 may be represented by the following Chemical Formula 2 or 3.

[Chemical Formula 2]

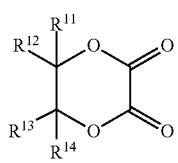

[Chemical Formula 3]

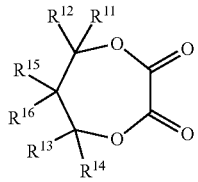

(In Chemical Formula 2 or 3, $R^{11}$ to $R^{16}$ are each independently hydrogen, cyano, halo (C1-C10)alkyl, (C1-C10)alkyl, (C1-C10)alkoxy, or (C1-C10)alkoxycarbonyl.)

The compound represented by Chemical Formula 1 may be selected from compounds having the following structures, but is not limited thereto.

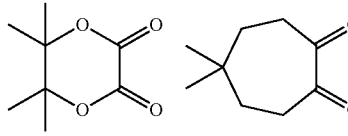

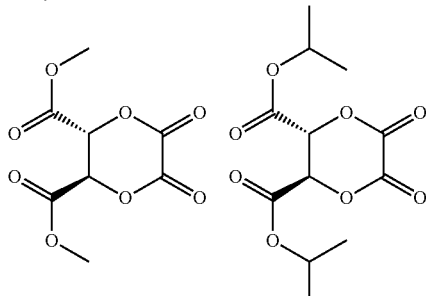

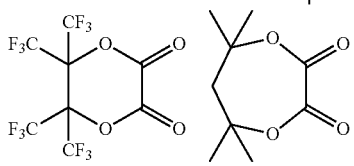

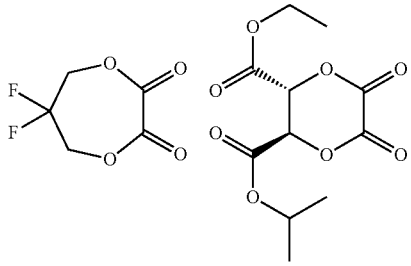

The compound represented by Chemical Formula 1 may be contained at a content of 0.1 to 5 wt % based on a total weight of the electrolyte.

The electrolyte may further contain one or two or more additional additives selected from the group consisting of oxalatoborate based compounds, carbonate based compounds substituted with fluorine, vinylidene carbonate based compounds, and compounds containing a sulfinyl group.

The electrolyte may further contain one or more additional additives selected from the group consisting of lithium difluoro(oxalato)borate (LiFOB), lithium bis(oxalato)borate (LiB($C_2O_4$)$_2$, LiBOB), fluoroethylene carbonate (FEC), vinylene carbonate (VC), vinylethylene carbonate (VEC), divinyl sulfone, ethylene sulfite, propylene sulfite, diallyl sulfonate, ethane sultone, propane sultone (PS), butane sultone, ethene sultone, butene sultone, and propene sultone (PRS).

The additional additive may be contained at a content of 0.1 to 5.0 wt % based on a total weight of the electrolyte.

The non-aqueous organic solvent may be selected from cyclic carbonate based solvents, linear carbonate based solvent, and a mixed solvent thereof, wherein the cyclic carbonate may be selected from the group consisting of ethylene carbonate, propylene carbonate, butylene carbonate, vinylene carbonate, vinylethylene carbonate, fluoroethylene carbonate, and a mixture thereof, and the linear carbonate may be selected from the group consisting of dimethyl carbonate, diethyl carbonate, dipropyl carbonate, ethyl methyl carbonate, methyl propyl carbonate, methyl isopropyl carbonate, ethyl propyl carbonate, and a mixture thereof.

The non-aqueous organic solvent may be a mixed solvent in which the linear carbonate solvent and the cyclic carbonate solvent are mixed at a mixed volume ratio of 1 to 9:1.

The lithium salt may be one or two or more selected from the group consisting of $LiPF_6$, $LiBF_4$, $LiClO_4$, $LiSbF_6$, $LiAsF_6$, $LiN(SO_2C_2F_5)_2$, $LiN(CF_3SO_2)_2$, $LiN(SO_3C_2F_5)_2$, $LiN(SO_2F)_2$, $LiCF_3SO_3$, $LiC_4F_9SO_3$, $LiC_6H_5SO_3$, LiSCN, $LiAlO_2$, $LiAlCl_4$, $LiN(C_xF_{2x+1}SO_2)(C_yF_{2y+1}SO_2)$ (here, x and y are natural numbers), LiCl, LiI, and $LiB(C_2O_4)_2$.

The lithium salt may be contained at a concentration of 0.1 to 2.0 M.

In another general aspect, a lithium secondary battery contains the electrolyte for a lithium secondary battery as described above.

DETAILED DESCRIPTION OF EMBODIMENTS

Hereinafter, the present invention will be described in more detail. Here, technical terms and scientific terms used in the present specification have the general meaning understood by those skilled in the art to which the present invention pertains unless otherwise defined, and a description for the known function and configuration unnecessarily obscuring the gist of the present invention will be omitted in the following description.

The present invention provides a novel compound represented by the following Chemical Formula 1, which may be used as an additive of a lithium secondary battery.

[Chemical Formula 1]

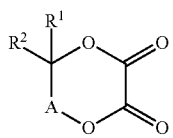

(In Chemical Formula 1, $R^1$ to $R^4$ are each independently hydrogen, cyano, halo (C1-C10)alkyl, (C1-C10)alkyl, (C1-C10)alkoxy, or (C1-C10)alkoxycarbonyl; and A is a single bond or $-(CR^3R^4)_n-$, n being an integer of 1 to 3.)

The novel compound represented by Chemical Formula 1 according to an exemplary embodiment in the present invention may be represented by the following Chemical Formula 2 or 3.

[Chemical Formula 2]

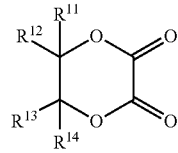

[Chemical Formula 3]

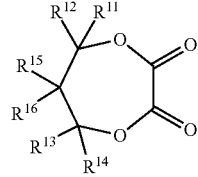

(In Chemical Formulas 2 and 3, $R^{11}$ to $R^{16}$ are each independently hydrogen, cyano, halo (C1-C10)alkyl, (C1-C10)alkyl, (C1-C10)alkoxy, or (C1-C10)alkoxycarbonyl.)

In Chemical Formulas 2 and 3, $R^{11}$ to $R^{16}$ may be each independently hydrogen, cyano, halo(C1-C10)alkyl, (C1-C10)alkyl, (C1-C10)alkoxy, or (C1-C10)alkoxycarbonyl.

Further, the present invention provides an electrolyte for a lithium secondary battery, containing the compound represented by the following Chemical Formula 1, in order to provide a battery having significantly excellent discharge capacity at a low temperature while having excellent high-temperature storage characteristics and life cycle characteristics.

That is, the present invention provides an electrolyte for a lithium secondary battery containing a lithium salt; a non-aqueous organic solvent; and the compound represented by the following Chemical Formula 1:

[Chemical Formula 1]

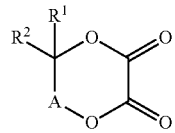

(in Chemical Formula 1, $R^1$ to $R^4$ are each independently hydrogen, cyano, halo (C1-C10)alkyl, (C1-C10)alkyl, (C1-C10)alkoxy, or (C1-C10)alkoxycarbonyl; and A is a single bond or $-(CR^3R^4)_n-$, n being an integer of 1 to 3.)

As the electrolyte for a secondary battery according to the present invention contains the compound represented by Chemical Formula 1, a capacity recovery rate at a high temperature may be high, and a thickness change rate may be low, such that the electrolyte may be more stable at a high temperature.

In more detail, the compound represented by Chemical Formula 1 according to the present invention may have a structure in which two oxygen atoms are contained in a ring of the heterocycloalkyl compound and two carbon atoms are substituted with carbonyl groups, and be decomposed at an anode to form a SEI film, such that the compound may increase stability at a high temperature while suppressing decomposition of a solvent, thereby making it possible to improve high-temperature and low-temperature characteristics.

In the electrolyte for a lithium secondary battery according to an exemplary embodiment of the present invention, the compound represented by Chemical Formula 1 may be represented by the following Chemical Formula 2 or 3.

[Chemical Formula 2]

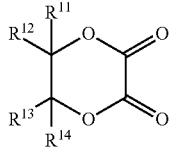

[Chemical Formula 3]

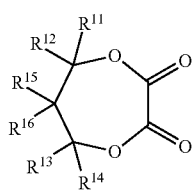

(In Chemical Formulas 2 and 3, $R^{11}$ to $R^{16}$ are each independently hydrogen, cyano, halo (C1-C10)alkyl, (C1-C10)alkyl, (C1-C10)alkoxy, or (C1-C10)alkoxycarbonyl.)

In Chemical Formulas 2 and 3, $R^{11}$ to $R^{16}$ may be each independently hydrogen, halo(C1-C10)alkyl, (C1-C10)alkyl, or (C1-C10)alkoxycarbonyl.

In view of chemical stability and electrical characteristics, preferably, the compound represented by Chemical Formula 1 is the compound represented by Chemical Formula 2, and in Chemical Formula 2, $R^{11}$ and $R^{13}$ may be hydrogen, and $R^{12}$ and $R^{14}$ may be each independently halo(C1-C10)alkyl, (C1-C10)alkyl, (C1-C10)alkoxy, or (C1-C10)alkoxycarbonyl.

More preferably, in Chemical Formula 2, $R^{11}$ and $R^{13}$ may be hydrogen, and $R^{12}$ and $R^{14}$ may be the same as each other and be halo(C1-C10)alkyl, (C1-C10)alkyl, or (C1-C10)alkoxycarbonyl.

In more detail, the compound represented by Chemical Formula 1 according to the present invention may be selected from compounds having the following structures, but is not limited thereto.

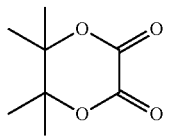 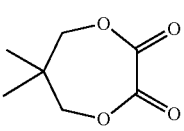

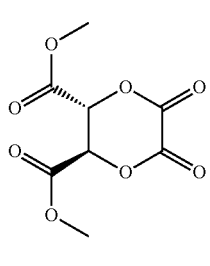 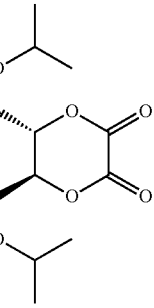

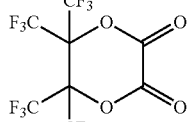

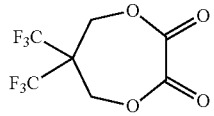

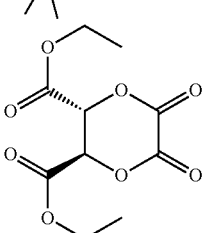

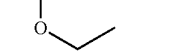

As disclosed herein, the terms ⌈alkyl⌋, ⌈alkoxy⌋, and other substituents including a ⌈alkyl⌋ part include both of the straight chain type and the branched chain type, and have 1 to 10 carbon atoms, preferably 1 to 6 carbon atoms, more preferably 1 to 4 carbon atoms.

As disclosed herein, the term "alkyl substituted with halogen or haloalkyl" means that at least one hydrogen existing in alkyl is substituted with halogen.

In the electrolyte for a lithium secondary battery according to an exemplary embodiment of the present invention, the compound represented by Chemical Formula 1 may be contained at a content of 0.1 to 5 wt % based on a total weight of the electrolyte for a lithium secondary battery. In view of high-temperature stability, it is more preferable that the compound is contained at a content of 1 to 3 wt %. When the content of the compound represented by Chemical Formula 1 is less than 0.1 wt %, addition effects such as improvement of high temperature stability or a capacity retention rate, or the like, are not exhibited, and an effect of improving discharge capacity, output, or the like, of the lithium secondary battery may be insufficient, and when the content of the compound is more than 5 wt %, characteristics of the lithium secondary battery may be rather deteriorated. For example, a life cycle of the lithium secondary battery is rapidly deteriorated.

In the electrolyte for a lithium secondary battery according to an exemplary embodiment of the present invention, the electrolyte may further contain one or two or more additives selected from the group consisting of oxalatoborate based compounds, carbonate based compounds substituted with fluorine, vinylidene carbonate based compounds, and compounds containing a sulfinyl group as an additional additive for improving the life cycle of the battery.

The oxalatoborate based compound may be a compound represented by the following Chemical Formula 11 or lithium bis(oxalato)borate (LiB(C$_2$O$_4$)$_2$, LiBOB).

[Chemical Formula 11]

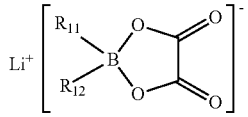

(In Chemical Formula 11, $R_{11}$ and $R_{12}$ are each independently halogen or halogenated (C1 to C10)alkyl.)

Specific examples of the oxalatoborate based additive may include lithium difluoro(oxalato)borate (LiB(C$_2$O$_4$)F$_2$, LiFOB), lithium bis(oxalato)borate (LiB(C$_2$O$_4$)$_2$, LiBOB), and the like.

The carbonate based compound substituted with fluorine may be fluoroethylene carbonate (FEC), difluoroethylene carbonate (DFEC), fluorodimethyl carbonate (FDMC), fluoroethyl methyl carbonate (FEMC), or a combination thereof.

The vinylidene carbonate based compound may be vinylene carbonate (VC), vinyl ethylene carbonate (VEC), or a mixture thereof.

The compound containing a sulfinyl (S=O) group may be sulfone, sulfite, sulfonate, and sultone (cyclic sulfonate), and the compound may be used alone or a mixture thereof may be used. In detail, the sulfone may be represented by the following Chemical Formula 12 and be divinyl sulfone. The sulfite may be represented by the following Chemical Formula 13 and be ethylene sulfite or propylene sulfite. The sulfonate may be represented by the following Chemical Formula 14 and be diallyl sulfonate. In addition, non-restrictive examples of sultone may include ethane sultone, propane sultone, butane sultone, ethene sultone, butene sultone, propene sultone, and the like.

[Chemical Formula 12]

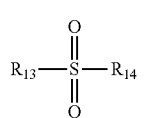

[Chemical Formula 13]

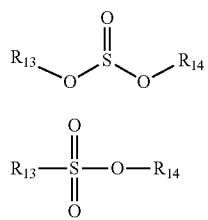

[Chemical Formula 14]

$$R_{13} - \overset{O}{\underset{O}{S}} - O - R_{14}$$

(In Chemical Formulas 12 to 14, R13 and R14 are each independently hydrogen, halogen, (C1-C10)alkyl, (C2-C10)alkenyl, (C1-C10)alkyl substituted with halogen, or (C2-C10)alkenyl substituted with halogen.)

More preferably, the electrolyte for a lithium secondary battery according to an exemplary embodiment of the present invention may further contain one or more additional additives selected from the group consisting of lithium difluoro(oxalato)borate (LiFOB), lithium bis(oxalato)borate (LiB($C_2O_4$)$_2$, LiBOB), fluoroethylene carbonate (FEC), vinylene carbonate (VC), vinylethylene carbonate (VEC), divinyl sulfone, ethylene sulfite, propylene sulfite, diallyl sulfonate, ethane sultone, propane sultone (PS), butane sultone, ethene sultone, butene sultone, and propene sultone (PRS). More preferably, the electrolyte may further contain one or two or more additives selected from lithium bis(oxalato)borate (LiB($C_2O_4$)$_2$, LiBOB), vinylene carbonate (VC), vinylethylene carbonate (VEC), ethylene sulfite, ethane sultone, and propane sultone (PS).

In the electrolyte for a lithium secondary battery according to an exemplary embodiment of the present invention, a content of the additional additive is not particularly limited, but in order to improve the life cycle of the battery, the additional additive may be contained in the electrolyte for a lithium secondary battery at a content of 0.1 to 5 wt %, more preferably 0.1 to 3 wt % based on the total weight of the electrolyte.

In the electrolyte for a lithium secondary battery according to an exemplary embodiment of the present invention, the non-aqueous organic solvent may include carbonate, ester, ether, or ketone alone, or a mixed solvent thereof, but it is preferable that the non-aqueous organic solvent is selected from cyclic carbonate based solvents, linear carbonate based solvents, and a mixed solvent thereof. It is most preferable to use a mixture of the cyclic carbonate based solvent and the linear carbonate based solvent. The cyclic carbonate solvent may sufficiently dissociate lithium ions due to large polarity, but has a disadvantage in that ion conductivity thereof is small due to a large viscosity. Therefore, characteristics of the lithium secondary battery may be optimized by mixing a linear carbonate solvent that has a small polarity and a low viscosity with the cyclic carbonate solvent.

The cyclic carbonate based solvent may be selected from the group consisting of ethylene carbonate, propylene carbonate, butylene carbonate, vinylene carbonate, vinylethylene carbonate, fluoroethylene carbonate, and a mixture thereof, and the linear carbonate based solvent may be selected from the group consisting of dimethyl carbonate, diethyl carbonate, dipropyl carbonate, ethyl methyl carbonate, methyl propyl carbonate, methyl isopropyl carbonate, ethyl propyl carbonate, and a mixture thereof.

In the electrolyte for a lithium secondary battery according to an exemplary embodiment of the present invention, in the non-aqueous organic solvent, which is the mixed solvent of the cyclic carbonate based solvent and the linear carbonate based solvent, a mixed volume ratio of the linear carbonate solvent and the cyclic carbonate solvent may be 1 to 9:1, preferably 1.5 to 4:1.

In the electrolyte for a high-voltage lithium secondary battery according to an exemplary embodiment of the present invention, the lithium salt may be one or two or more selected from the group consisting of LiPF$_6$, LiBF$_4$, LiClO$_4$, LiSbF$_6$, LiAsF$_6$, LiN(SO$_2$C$_2$F$_5$)$_2$, LiN(CF$_3$SO$_2$)$_2$, LiN(SO$_3$C$_2$F$_5$)$_2$, LiN(SO$_2$F)$_2$, LiCF$_3$SO$_3$, LiC$_4$F$_9$SO$_3$, LiC$_6$H$_5$SO$_3$, LiSCN, LiAlO$_2$, LiAlCl$_4$, LiN(C$_x$F$_{2x+1}$SO$_2$)(C$_y$F$_{2y+1}$SO$_2$) (here, x and y are natural numbers), LiCl, LiI, and LiB(C$_2$O$_4$)$_2$, but is not limited thereto.

The lithium salt may be used in a concentration range of preferably 0.1 to 2.0 M, and more preferably, 0.7 to 1.6 M. In the case in which the concentration of the lithium salt is less than 0.1 M, conductivity of the electrolyte is decreased, such that performance of the electrolyte is deteriorated, and in the case in which the concentration is more than 2.0 M, the viscosity of the electrolyte is increased, such that mobility of the lithium ion may be decreased. The lithium salt acts as a supply source of the lithium ion in the battery to enable a basic operation of the lithium secondary battery.

Since the electrolyte for a lithium secondary battery according to an exemplary embodiment of the present invention is stable in a temperature range of −20 to 60° C., and maintains electrochemically stable characteristics thereof even at a voltage of 4.4 V, the electrolyte may be applied to all of the lithium secondary batteries such as a lithium ion battery, a lithium polymer battery, and the like.

In addition, the present invention provides a lithium secondary battery containing the electrolyte for a lithium secondary battery.

A non-restrictive example of the secondary battery may include a lithium metal secondary battery, a lithium ion secondary battery, a lithium polymer secondary battery, a lithium ion polymer secondary battery, or the like.

The lithium secondary battery manufactured using the electrolyte for a lithium secondary battery according to the present invention is characterized in that a high-temperature storage efficiency is 75% or more and when the lithium secondary battery was kept at a high temperature for a long period of time, a thickness increase rate of the lithium secondary battery is significantly low (1 to 20%, more preferably 1 to 15%).

The lithium secondary battery according to the present invention includes a cathode and an anode.

It is preferable that the cathode contains a cathode active material capable of intercalating and deintercalating the lithium ion, and it is preferable that the cathode active material as described above is a complex metal oxide of lithium and at least one kind selected from cobalt, manganese, and nickel. A solid-solution ratio between the metals may be various, and an element selected from the group consisting of Mg, Al, Co, K, Na, Ca, Si, Ti, Sn, V, Ge, Ga, B, As, Zr, Mn, Cr, Fe, Sr, V, and rare earth elements may be further contained in the cathode active material as well as the above-mentioned metals. As a specific example of the cathode active material, a compound represented by any one of the following Chemical Formulas may be used:

$Li_aA_{1-b}B_bD_2$ (here, $0.90 \leq a \leq 1.8$ and $0 \leq b \leq 0.5$); $Li_aE_{1-b}B_bO_{2-c}D_c$ (here, $0.90 \leq a \leq 1.8$, $0 \leq b \leq 0.5$, and $0 \leq c \leq 0.05$); $LiE_{2-b}B_bO_{4-c}D_c$ (here, $0 \leq b \leq 0.5$ and $0 \leq c \leq 0.05$); $Li_aNi_{1-b-c}Co_bB_cD_\alpha$ (here, $0.90 \leq a \leq 1.8$, $0 \leq b \leq 0.5$, $0 \leq c \leq 0.05$, and $0 < \alpha \leq 2$); $Li_aNi_{1-b-c}Co_bB_cO_{2-\alpha}F_\alpha$ (here, $0.90 \leq a \leq 1.8$, $0 \leq b \leq 0.5$, $0 \leq c \leq 0.05$, and $0 < \alpha < 2$); $Li_aNi_{1-b-c}Co_bB_cO_{2-\alpha}F_2$ (here, $0.90 \leq a \leq 1.8$, $0 \leq b \leq 0.5$, $0 \leq c \leq 0.05$, and $0 < \alpha < 2$); $Li_aNi_{1-b-c}Mn_bB_cD_\alpha$ (here, $0.90 \leq a \leq 1.8$, $0 \leq b \leq 0.5$, $0 \leq c \leq 0.05$, and $0 < \alpha \leq 2$); $Li_aNi_{1-b-c}Mn_bB_cO_{2-\alpha}F_\alpha$ (here, $0.90 \leq a \leq 1.8$, $0 \leq b \leq 0.5$, $0 \leq c \leq 0.05$, and $0 < \alpha < 2$); $Li_aNi_{1-b-c}Mn_bB_cO_{2-\alpha}F_2$ (here, $0.90 \leq a \leq 1.8$, $0 \leq b \leq 0.5$, $0 \leq c \leq 0.05$, and $0 < \alpha < 2$); $Li_aN_{i_b}E_cG_dO_2$ (here, $0.90 \leq a \leq 1.8$, $0 \leq b \leq 0.9$, $0 \leq c \leq 0.5$, and $0.001 \leq d \leq 0.1$); $Li_aNi_bCo_cMn_dGeO_2$ (here, $0.90 \leq a \leq 1.8$, $0 \leq b \leq 0.9$, $0 \leq c \leq 0.5$, $0 \leq d \leq 0.5$, and $0.001 \leq e \leq 0.1$); $Li_aNiG_bO_2$ (here, $0.90 \leq a \leq 1.8$ and $0.001 \leq b \leq 0.1$); $Li_aCoG_bO_2$ (here, $0.90 \leq a \leq 1.8$ and $0.001 \leq b \leq 0.1$); $Li_aMnG_bO_2$ (here, $0.90 \leq a \leq 1.8$ and $0.001 \leq b \leq 0.1$); $Li_aMn_2G_bO_4$ (here, $0.90 \leq a \leq 1.8$ and $0.001 \leq b \leq 0.1$); $QO_2$; $QS_2$; $LiQS_2$; $V_2O_5$; $LiV_2O_5$; $LiIO_2$; $LiNiVO_4$; $Li_{(3-f)}J_2(PO_4)_3$ ($0 \leq f \leq 2$); $Li_{(3-f)}Fe_2(PO_4)_3$ ($0 \leq f \leq 2$); and $LiFePO_4$.

In the Chemical Formulas, A may be Ni, Co, Mn, or a combination thereof; B may be Al, Ni, Co, Mn, Cr, Fe, Mg, Sr, V, a rare earth element, or a combination thereof; D may be O, F, S, P, or a combination thereof; E may be Co, Mn, or a combination thereof; F may be F, S, P, or a combination thereof; G may be Al, Cr, Mn, Fe, Mg, La, Ce, Sr, V, or a combination thereof; Q may be Ti, Mo, Mn, or a combination thereof; I may be Cr, V, Fe, Sc, Y, or a combination thereof; and J may be V, Cr, Mn, Co, Ni, Cu, or a combination thereof.

The anode contains an anode active material capable of intercalating and deintercalating the lithium ion, and as this anode active material, a carbon material such as crystalloid carbon, amorphous carbon, carbon complex, a carbon fiber, or the like, a lithium metal, an alloy of lithium and another element, or the like, may be used. Examples of the amorphous carbon may include hard carbon, coke, mesocarbon microbead (MCMB) sintered at a temperature of 1500° C. or less, mesophase pitch-based carbon fiber (MPCF), and the like. Examples of the crystalloid carbon include graphite based materials, more specifically, natural graphite, graphitized coke, graphitized MCMB, graphitized MPCF, and the like. As the carbon material, a material of which an interplanar distance is 3.35 to 3.38 Å, and a crystallite size Lc measured by X-ray diffraction is at least 20 nm or more may be preferable. Another element forming the alloy with lithium may be aluminum, zinc, bismuth, cadmium, antimony, silicon, lead, tin, gallium, or indium.

The cathode or anode may be prepared by dispersing an electrode active material, a binder, and a conductive material, and if necessary, a thickener, in a solvent to prepare an electrode slurry composition, and applying this electrode slurry composition onto an electrode current collector. As a cathode current collector, aluminum, an aluminum alloy, or the like, may be mainly used, and as an anode current collector, copper, a copper alloy, or the like, may be mainly used. The cathode current collector and the anode current collector have a foil or mesh shape.

The binder is a material playing a role in paste formation of the active material, adhesion between the active materials, adhesion with the current collector, and a buffering effect on expansion and contraction of the active material, and the like. Examples of the binder may include polyvinylidene fluoride (PVdF), a polyhexafluoropropylene-polyvinylidene fluoride (PVdF/HFP) copolymer, poly(vinylacetate), polyvinyl alcohol, polyethyleneoxide, polyvinylpyrrolidone, alkylated polyethyleneoxide, polyvinyl ether, poly(methylmethacrylate), poly(ethylacrylate), polytetrafluoroethylene, polyvinylchloride, polyacrylonitrile, polyvinylpyridine, styrene-butadiene rubber, acrylonitrile-butadiene rubber, and the like. A content of the binder is 0.1 to 30 wt %, preferably 1 to 10 wt % based on the electrode active material. In the case in which the content of the binder is excessively low, adhesive force between the electrode active material and the current collector may become insufficient, and in the case in which the content is excessively high, adhesive force may be improved, but a content of the electrode active material is decreased in accordance with the content of the binder, which is disadvantageous in allowing the battery to have high capacity.

The conductive material is used to impart conductivity to the electrode, and any electronic conductive material may be used as long as it does not cause a chemical change in a battery to be configured. At least one selected from the group consisting of a graphite based conductive material, a carbon black based conductive material, and a metal or metal compound based conductive material may be used. Examples of the graphite based conductive material may include artificial graphite, natural graphite, and the like, examples of the carbon black based conductive material may include acetylene black, Ketjen black, Denka black, thermal black, channel black, and the like, and examples of the metal or metal compound based conductive material may include tin, tin oxide, tin phosphate ($SnPO_4$), titanium oxide, potassium titanate, a perovskite material such as $LaSrCoO_3$ and $LaSrMnO_3$. However, the conductive material is not limited thereto.

A content of the conductive material is preferably 0.1 to 10 wt % based on the electrode active material. In the case in which the content of the conductive material is less than 0.1 wt %, electrochemical properties may be deteriorated, and in the case in which the content is more than 10 wt %, energy density per weight may be decreased.

Any thickener may be used without limitation as long as it may serve to adjust a viscosity of the active material slurry, but for example, carboxymethyl cellulose, hydroxymethyl cellulose, hydroxyethyl cellulose, hydroxypropyl cellulose, or the like, may be used.

As the solvent in which the electrode active material, the binder, the conductive material, and the like, are dispersed, a non-aqueous solvent or aqueous solvent may be used. Examples of the non-aqueous solvent may include N-methyl-2-pyrrolidone (NMP), dimethylformamide, dimethylacetamide, N,N-dimethylaminopropylamine, ethyleneoxide, tetrahydrofuran, or the like.

The lithium secondary battery according to the present invention may include a separator preventing a short-circuit between the cathode and the anode and providing a movement path of the lithium ion. As the separator as described above, a polyolefin based polymer membrane made of polypropylene, polyethylene, polyethylene/polypropylene, polyethylene/polypropylene/polyethylene, polypropylene/polyethylene/polypropylene, or the like, or a multilayer thereof, a micro-porous film, and woven fabric and non-woven fabric may be used. In addition, a film in which a resin having excellent stability is coated on a porous polyolefin film may be used.

The lithium secondary battery according to the present invention may have various shapes such as a cylindrical shape, a pouch shape, in addition to an angular shape.

Hereinafter, Examples and Comparative Examples of the present invention will be described. However, the following Example is only a preferable example of the present invention, and the present invention is not limited thereto. Under the assumption that the lithium salt is entirely dissociated so that a concentration of lithium ion becomes 1 M, a base electrolyte may be formed by dissolving a corresponding amount of the lithium salt such as $LiPF_6$ in a basic solvent so as to have a concentration of 1 M.

EXAMPLE 1

Synthesis of
5,5,6,6-tetramethyl-1,4-dioxane-2,3-dione
(hereinafter, referred to as 'PEA77')

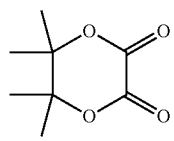

After 2.36 g of pinacol (20 mmol) and 4.75 g of pyridine (60 mmol) were dissolved in 30 ml of tetrahydrofuran (THF) in a 100 ml round bottom flask, a temperature was lowered to 0° C. 3.05 g of oxalyl chloride (24 mmol) was slowly added thereto for 30 minutes under $N_2$ atmosphere, and the temperature was raised to room temperature. After a reaction was carried out at room temperature for 15 minutes, the reaction was terminated by adding 30 ml of distilled water. An organic layer was collected by extracting the resultant with 20 ml of ethyl acetate two times, washed with 20 ml of 1N HCl solution once, and then washed with 20 ml of saturated aqueous sodium bicarbonate ($NaHCO_3$) solution once. After the organic layer was dried over anhydrous magnesium sulfate ($MgSO_4$) and concentrated, the remaining solid was recrystallized in a mixed solvent of ethyl acetate and hexane, thereby obtaining the title compound (2.0 g).

$^1$H-NMR (400 MHz, $CDCl_3$) δ: 1.55 (s, 12H)

EXAMPLE 2

Synthesis of 6,6-dimethyl-[1,4]dioxepane-2,3-dione
(hereinafter, referred to as 'PEA79')

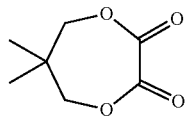

After 2.08 g of 2,2-dimethyl-1,3-propanediol (20 mmol) and 4.75 g of pyridine (60 mmol) were dissolved in 30 ml of tetrahydrofuran (THF) in a 100 ml round bottom flask, a temperature was lowered to 0° C. 3.05 g of oxalyl chloride (24 mmol) was slowly added thereto for 30 minutes under $N_2$ atmosphere, and the temperature was raised to room temperature. After a reaction was carried out at room temperature for 15 minutes, the reaction was terminated by adding 30 ml of distilled water. An organic layer was collected by extracting the resultant with 20 ml of ethyl acetate two times, washed with 20 ml of 1N HCl solution once, and then washed with 20 ml of saturated aqueous sodium bicarbonate ($NaHCO_3$) solution once. After the organic layer was dried over anhydrous magnesium sulfate ($MgSO_4$) and concentrated, the remaining solid was reslurried in diethylether, and filtered. The remaining solid after filtering was washed with 10 ml of diethylether two times, and dried under vacuum, thereby obtaining the title compound (1.4 g).

$^1$H-NMR (400 MHz, $CDCl_3$) δ: 4.09 (s, 4H), 1.05 (s, 6H)

EXAMPLE 3

Synthesis of (2R,3R)-diethyl
5,6-dioxo-1,4-dioxane-2,3-dicarboxylate
(hereinafter, referred to as 'PEA82')

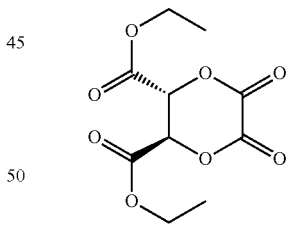

After 4.12 g of diethyl-L-tartrate (20 mmol) and 4.75 g of pyridine (60 mmol) were dissolved in 30 ml of tetrahydrofuran (THF) in a 100 ml round bottom flask, a temperature was lowered to 0° C. 3.05 g of oxalyl chloride (24 mmol) was slowly added thereto for 30 minutes under $N_2$ atmosphere, and the temperature was raised to room temperature. After a reaction was carried out at room temperature for 15 minutes, the reaction was terminated by adding 30 ml of distilled water. An organic layer was collected by extracting the resultant with 20 ml of ethyl acetate two times, washed with 20 ml of 1N HCl solution once, and then washed with 20 ml of saturated aqueous sodium bicarbonate ($NaHCO_3$) solution once. After the organic layer was dried over anhydrous magnesium sulfate ($MgSO_4$) and concentrated, the remaining solid was recrystallized in a mixed solvent of ethyl acetate and hexane, thereby obtaining the title compound (1.4 g).

$^1$H-NMR (400 MHz, CDCl$_3$) δ: 5.86 (s, 2H), 4.32-4.19 (m, 4H), 1.24 (q, J=7.2 Hz, 6H)

EXAMPLE 4

Synthesis of (2R,3R)-diisopropyl 5,6-dioxo-1,4-dioxane-2,3-dicarboxylate (hereinafter, referred to as 'PEA88')

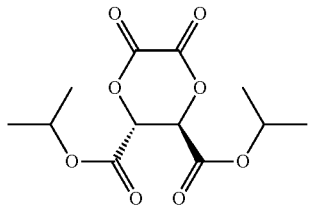 [SMILES: CC(C)OC(=O)[C@@H]1OC(=O)C(=O)O[C@H]1C(=O)OC(C)C]

After 4.69 g of diisopropyl-L-tartrate (20 mmol) and 4.75 g of pyridine (60 mmol) were dissolved in 30 ml of tetrahydrofuran (THF) in a 100 ml round bottom flask, a temperature was lowered to 0° C. 3.05 g of oxalyl chloride (24 mmol) was slowly added thereto for 30 minutes under N$_2$ atmosphere, and the temperature was raised to room temperature. After a reaction was carried out at room temperature for 15 minutes, the reaction was terminated by adding 30 ml of distilled water. An organic layer was collected by extracting the resultant with 20 ml of ethyl acetate two times, washed with 20 ml of 1N HCl solution once, and then washed with 20 ml of saturated aqueous sodium bicarbonate (NaHCO$_3$) solution once. After the organic layer was dried over anhydrous magnesium sulfate (MgSO$_4$) and concentrated, the remaining solid was recrystallized in a mixed solvent of tetrahydrofuran and diethylether, thereby obtaining the title compound (1.7 g).

$^1$H-NMR (400 MHz, CDCl$_3$) δ: 5.84 (s, 2H), 4.32-4.19 (sep, J=5.2, 2H), 1.26 (d, J=5.2 Hz, 6H), 1.20 (d, J=4.8 Hz, 6H)

EXAMPLE 5

Synthesis of 5,5,6,6-tetrakis(trifluoromethyl)-1,4-dioxane-2,3-dione (hereinafter, referred to as 'PEA78')

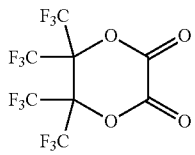

After 6.68 g of hexafluoro-2,3-bis(trifluoromethyl)-2,3-butanediol (20 mmol) and 4.75 g of pyridine (60 mmol) were dissolved in 30 ml of tetrahydrofuran (THF) in a 100 ml round bottom flask, a temperature was lowered to 0° C. 3.05 g of oxalyl chloride (24 mmol) was slowly added thereto for 30 minutes under N$_2$ atmosphere, and the temperature was raised to room temperature. After a reaction was carried out at room temperature for 15 minutes, the reaction was terminated by adding 30 ml of distilled water. An organic layer was collected by extracting the resultant with 20 ml of ethyl acetate two times, washed with 20 ml of 1N HCl solution once, and then washed with 20 ml of saturated aqueous sodium bicarbonate (NaHCO$_3$) solution once. After the organic layer was dried over anhydrous magnesium sulfate (MgSO$_4$) and concentrated, the remaining solid was recrystallized in a mixed solvent of ethyl acetate and hexane, thereby obtaining the title compound (3.2 g).

EXAMPLES 6 to 15 and COMPARATIVE EXAMPLES 1 and 2

A solution obtained by dissolving LiPF$_6$ in a mixed solvent in which ethylene carbonate (EC) and ethyl methyl carbonate (EMC) were mixed at a volume ratio of 3:7 so as to have a concentration of 1.0 M was used as a basic electrolyte (1M LiPF$_6$, EC/EMC=3:7), and ingredients shown in the following Table 1 were additionally injected, thereby preparing electrolytes.

A battery to which the non-aqueous electrolyte was applied was manufactured as follows.

After mixing LiNiCoMnO$_2$ and LiMn$_2$O$_4$ at a weight ratio of 1:1 as a cathode active material, the cathode active material, polyvinylidene fluoride (PVdF) as a binder, and carbon as a conductive material were mixed at a weight ratio of 92:4:4 and then dispersed in N-methyl-2-pyrrolidone, thereby preparing cathode slurry. This slurry was coated on aluminum foil having a thickness of 20 μm, dried, and rolled, thereby preparing a cathode. After artificial graphite as an anode active material, styrene-butadiene rubber as a binder, and carboxymethyl cellulose as a thickener were mixed at a weight ratio of 96:2:2, the mixture was dispersed in water, thereby preparing anode active material slurry. This slurry was coated on copper foil having a thickness of 15 μm, dried, and rolled, thereby preparing an anode.

A film separator made of a polyethylene (PE) material and having a thickness of 25 μm was stacked between the manufactured electrodes, and a cell was configured using a pouch having a size of 8 mm×270 mm×185 mm (thickness× width×length), followed by injection of the non-aqueous electrolyte, thereby manufacturing a 25 Ah-class lithium secondary battery for an electric vehicle (EV).

Performance of the 25 Ah-class lithium secondary battery for an electric vehicle (EV) manufactured as described above was evaluated as follows. Evaluation items are as follows.

*Evaluation Item*

1. 1 C Discharge capacity at −20° C.: After the battery was charged at room temperature for 3 hours (25 A, 4.2 V constant current-constant voltage (CC-CV)), the battery was kept at −20° C. for 4 hours, and then, the battery was discharged to 2.7 V (25 A, CC). Thereafter, usable capacity (%) with respect to initial capacity was measured.

2. Capacity Recovery Rate after 30 Days at 60° C.: After charging the battery at room temperature for 3 hours (25 A, 4.2 V CC-CV), the battery was kept at 60° C. for 30 days, and then, the battery was discharged to 2.7 V (25 A, CC). Thereafter, a recovery rate (%) with respect to initial capacity was measured.

3. Thickness Increase Rate after 30 days at 60° C.: When a thickness of the battery after charging the battery at room temperature for 3 hours (12.5 A, 4.4 V CC-CV) was defined as A and a thickness of the battery kept at 60° C. and an atmospheric pressure exposed in the air for 30 days using a closed thermostatic device was defined as B, a thickness increase rate was calculated by the following Equation 1.

$$(B-A)/A \times 100 (\%) \quad \text{[Equation 1]}$$

4. Life Cycle at Room Temperature A process of charging the battery at room temperature (50 A, 4.2V, CC-CV) for 3 hours and then discharging the battery to 2.7V (2.7V, 25 A) was repeated 500 times. In this case, discharge capacity at a first time was defined as C, and discharge capacity at a 500th time was divided by the discharge capacity C at the first time, thereby calculating a capacity retention rate during the life cycle.

TABLE 1

| | Electrolyte Composition | After 30 days at 60° C. | | Capacity Retention Rate during Life Cycle | Discharge Capacity at −20° C. |
| --- | --- | --- | --- | --- | --- |
| | | Capacity Recovery Rate | Thickness Increase Rate | | |
| Example 6 | Basic Electrolyte + PEA77 1 wt % | 78% | 11% | 81% | 85% |
| Example 7 | Basic Electrolyte + PEA78 1 wt % | 79% | 12% | 71% | 88% |
| Example 8 | Basic Electrolyte + PEA79 1 wt % | 82% | 9% | 75% | 77% |
| Example 9 | Basic Electrolyte + PEA82 1 wt % | 83% | 8% | 86% | 89% |
| Example 10 | Basic Electrolyte + PEA88 1 wt % | 86% | 7% | 88% | 89% |
| Example 11 | Basic Electrolyte + PEA88 0.5 wt % | 84% | 10% | 85% | 88% |
| Example 12 | Basic Electrolyte + PEA88 3 wt % | 89% | 5% | 83% | 83% |
| Example 13 | Basic Electrolyte + PEA88 1 wt % + VC 1 wt % | 88% | 8% | 90% | 86% |
| Example 14 | Basic Electrolyte + PEA88 1 wt % + VC 1 wt % + PS 1 wt % | 91% | 1% | 91% | 87% |
| Example 15 | Basic Electrolyte + PEA88 1 wt % + VC 1 wt % + LiBOB 1 wt % | 92% | 2% | 92% | 88% |
| Comparative Example 1 | Basic Electrolyte | 37% | 30% | 20% | 55% |
| Comparative Example 2 | Basic Electrolyte + VC 1 wt % + PS 1 wt % | 60% | 12% | 61% | 48% |

Basic Electrolyte: 1M LiPF$_6$, EC/EMC = 3:7
LiBOB: Lithium-bis(Oxalato)Borate
VC: Vinylene carbonate
PS: 1,3-propane sultone As shown in Table 1, it may be appreciated that the lithium secondary battery containing the electrolyte for a lithium secondary battery according to the present invention had a high capacity recovery rate after 30 days at 60° C., and the thickness increase rate was significantly low, such that high-temperature stability was significantly high.

On the contrary, it may be appreciated that in the case of the electrolyte for a lithium secondary battery that did not contain the compound represented by Chemical Formula 1 according to the present invention, high-temperature capacity recovery rate was low, and the thickness increase rate thereof was also significantly high (30%), such that high-temperature stability was deteriorated.

Further, it may be appreciated that in the lithium secondary battery according to the present invention, containing the electrolyte for a lithium secondary battery containing the compound represented by Chemical Formula 1, discharge capacity at −20° C. and a capacity retention rate during the life cycle were also high, such that low-temperature characteristics were excellent.

Therefore, the compound represented by Chemical Formula 1 according to the present invention may also improve high-temperature stability and low-temperature discharge capacity.

In addition, the electrolyte for a secondary battery according to the present invention further contains the compound represented by Chemical Formula 1 according to the present invention and at least one additive selected from lithium bis(oxalato)borate (LiB(C$_2$O$_4$)$_2$, LiBOB), vinylene carbonate (VC), vinylethylene carbonate (VEC), ethylene sulfite, ethane sultone, propane sultone (PS), such that high-temperature storage stability, low-temperature discharge capacity, and life cycle characteristics may be further improved. Therefore, the lithium secondary battery containing the electrolyte for a secondary battery according to the present invention may have significantly high efficiency and stability, and excellent life cycle characteristics.

The novel compound according to the present invention may be contained in the electrolyte for a lithium secondary battery, thereby improving the characteristics of the lithium secondary battery containing the electrolyte for a lithium secondary battery.

The electrolyte for a lithium secondary battery according to the present invention contains the heterocycloalkyl compound containing two oxygen atoms, such that a swelling phenomenon that the battery is swelled at a high temperature may be significantly decreased, and thus, the electrolyte may have excellent high-temperature storage characteristics.

Further, the electrolyte for a lithium secondary battery according to the present invention contains the heterocycloalkyl compound in which two oxygen atoms are contained in the ring and two carbon atoms in the ring are substituted with carbonyl groups, thereby making it possible to significantly increase low-temperature discharge capacity as well as the high-temperature capacity recovery rate.

In addition, the electrolyte for a lithium secondary battery according to the present invention further contains the compound represented by Chemical Formula 1 and one or two or more additional additives selected from the group consisting of the oxalatoborate based compounds, the carbonate based compounds substituted with fluorine, the vinylidene carbonate based compounds, and the compounds containing a sulfinyl group, such that the electrolyte may have more excellent life cycle characteristics, high-temperature stability, and low-temperature characteristics.

Furthermore, the lithium secondary battery according to the present invention uses the electrolyte for a lithium secondary battery according to the present invention, containing the compound represented by Chemical Formula 1, such that the lithium secondary battery has excellent high-temperature storage stability and low-temperature characteristics while maintaining excellent basic performance such as high-efficiency charge and discharge characteristics, life cycle characteristics, and the like.

Although the exemplary embodiments of the present invention have been disclosed in detail, those skilled in the art will appreciate that various modifications are possible, without departing from the scope and spirit of the invention as disclosed in the accompanying claims. Accordingly, such modifications of the exemplary embodiment of the present invention should also be understood to fall within the scope of the present invention.

What is claimed is:

1. An electrolyte for a secondary battery comprising:
a lithium salt;
a non-aqueous organic solvent; and
a compound represented by the following Chemical Formula 1:

[Chemical Formula 1]

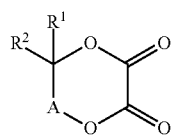

(In Chemical Formula 1,
$R^1$ to $R^4$ are each independently hydrogen, cyano, halo (C1-C10)alkyl, (C1-C10)alkyl, (C 1-C10)alkoxy, or (C1-C10)alkoxycarbonyl; and
A is a single bond or —$(CR^3R^4)_n$—, n being an integer of 1 to 3
wherein at least one of the $R^1$ and $R^2$ is $(C_1-C_{10})$alkoxycarbonyl or halo$(C_1-C^{10})$alkyl; and
at least one of the $R^3$ and $R^4$ is $(C_1-C_{10})$alkoxycarbonyl or halo$(C_1-C_{10})$alkyl).

2. The electrolyte for a secondary battery of claim 1, wherein the compound represented by Chemical Formula 1 is represented by the following Chemical Formula 2 or 3

[Chemical Formula 2]

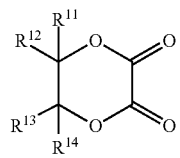

[Chemical Formula 3]

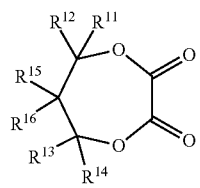

(In Chemical Formula 2 or 3,
$R^{11}$ to $R^{16}$ are each independently hydrogen, cyano, halo (C1-C10)alkyl, (C1-C10)alkyl, (C1-C10)alkoxy, or (C1-C10)alkoxycarbonyl)
wherein at least one of the $R^{11}$ and $R^{12}$ is $(C_1-C_{10})$ alkoxycarbonyl or halo$(C_1-C_{10})$alkyl;
at least one of the $R^{13}$ and $R^{14}$ is $(C_1-C_{10})$alkoxycarbonyl or halo$(C_1-C_{10})$alkyl;
at least one of the $R^{15}$ and $R^{16}$ is $(C_1-C_{10})$alkoxycarbonyl or halo$(C_1-C_{10})$alkyl;
$R^{13}$=$R^{15}$; and $R^{14}$=$R^{16}$.

3. The electrolyte for a secondary battery of claim 1, wherein the compound represented by Chemical Formula 1 is selected from compounds having the following structures

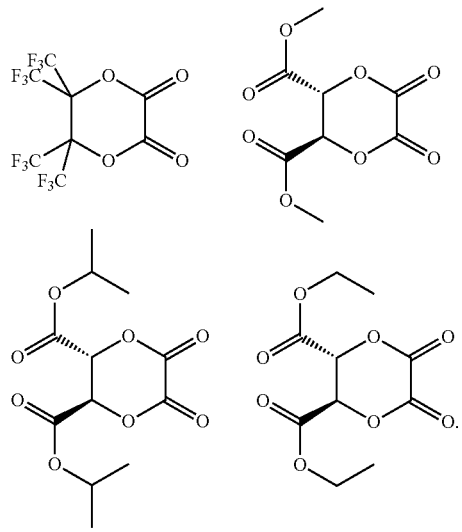

4. The electrolyte for a secondary battery of claim 1, wherein the compound represented by Chemical Formula 1 is contained at a content of 0.1 to 5 wt % based on a total weight of the electrolyte.

5. The electrolyte for a secondary battery of claim 1, further comprising one or two or more additives selected from the group consisting of oxalatoborate based compounds, carbonate based compounds substituted with fluorine, vinylidene carbonate based compounds, and compounds containing a sulfinyl group.

6. The electrolyte for a secondary battery of claim 5, wherein the one or two additives is/are selected from selected from the group consisting of lithium difluoro(oxalato)borate (LiFOB), lithium bis(oxalato)borate (LiB$(C_2O_4)_2$,LiBOB), fluoroethylene carbonate (FEC), vinylene carbonate (VC), vinylethylene carbonate (VEC), divinyl sulfone, ethylene sulfite, propylene sulfite, diallyl sulfonate, ethane sultone, propane sultone (PS), butane sultone, ethene sultone, butene sultone, and propene sultone (PRS).

7. The electrolyte for a secondary battery of claim 5, wherein the additive is contained at a content of 0.1 to 5.0 wt % based on a total weight of the electrolyte.

8. The electrolyte for a secondary battery of claim 1, wherein the non-aqueous organic solvent is selected from cyclic carbonate based solvents, linear carbonate based solvents, and a mixed solvent thereof.

9. The electrolyte for a secondary battery of claim 8, wherein the cyclic carbonate is selected from the group consisting of ethylene carbonate, propylene carbonate, butylene carbonate, vinylene carbonate, vinylethylene carbonate, fluoroethylene carbonate, and a mixture thereof, and the linear carbonate is selected from the group consisting of dimethyl carbonate, diethyl carbonate, dipropyl carbonate, ethyl methyl carbonate, methyl propyl carbonate, methyl isopropyl carbonate, ethyl propyl carbonate, and a mixture thereof.

10. The electrolyte for a secondary battery of claim 8, wherein the non-aqueous organic solvent is a mixed solvent in which the linear carbonate solvent and the cyclic carbonate solvent are mixed at a mixed volume ratio of 1 to 9:1.

11. The electrolyte for a secondary battery of claim 1, wherein the lithium salt is one or two or more selected from the group consisting of $LiPF_6$, $LiBF_4$, $LiClO_4$, $LiSbF_6$, $LiAsF_6$, $LiN(SO_2C_2F_5)_2$, $LiN(CF_3SO_2)_2$, $LiN(SO_3C_2F_5)_2$, $LiN(SO_2F)_2$, $LiCF_3SO_3$, $LiC_4F_9SO_3$, $LiC_6H_5SO_3$, LiSCN, $LiAlO_2$, $LiAlCl_4$, $LiN(C_xF_{2x+1}SO_2)(C_yF_{2y+1}SO_2)$ (here, x and y are natural numbers), LiCl, LiI, and $LiB(C_2O_4)_2$.

12. The electrolyte for a secondary battery of claim 1, wherein the lithium salt is contained at a concentration of 0.1 to 2.0 M.

13. A lithium secondary battery comprising the electrolyte for a secondary battery of claim 1.

14. A lithium secondary battery comprising the electrolyte for a secondary battery of claim 2.

* * * * *